(12) United States Patent
Flohr et al.

(10) Patent No.: US 8,121,377 B2
(45) Date of Patent: Feb. 21, 2012

(54) METHOD AND TOMOGRAPHY SCANNER FOR NORMALIZING IMAGE DATA WITH RESPECT TO A CONTRAST IN THE IMAGE DATA PRODUCED BY A CONTRAST AGENT

(75) Inventors: Thomas Flohr, Uehlfeld (DE); Bernhard Krauss, Burgthann (DE); Bernhard Schmidt, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 469 days.

(21) Appl. No.: 12/453,105

(22) Filed: Apr. 29, 2009

(65) Prior Publication Data

US 2009/0274358 A1  Nov. 5, 2009

(30) Foreign Application Priority Data

Apr. 30, 2008 (DE) .......................... 10 2008 021 835

(51) Int. Cl.
*G06K 9/00* (2006.01)
(52) U.S. Cl. ....................................................... 382/131
(58) Field of Classification Search .................. 382/128, 382/131, 154
See application file for complete search history.

(56) References Cited

U.S. PATENT DOCUMENTS

| | | | | |
|---|---|---|---|---|
| 4,551,800 A * | 11/1985 | Riederer et al. | ............... | 600/407 |
| 6,224,553 B1 * | 5/2001 | Nevo | ............................. | 600/437 |
| 6,468,505 B1 | 10/2002 | Lang | | |
| 7,321,674 B2 * | 1/2008 | Vuylsteke | ..................... | 382/128 |
| 2008/0095422 A1 * | 4/2008 | Suri et al. | ...................... | 382/131 |

* cited by examiner

*Primary Examiner* — Roy M Punnoose
(74) *Attorney, Agent, or Firm* — Harness, Dickey & Pierce, P.L.C.

(57) ABSTRACT

A method and a correspondingly configured tomography scanner are disclosed for normalizing image data with respect to a contrast in the image data produced by a contrast agent, the image data illustrating a tissue structure to be examined and at least part of a blood vessel system of an examination region connected to the tissue structure, which are at least in part permeated by the contrast agent. In an embodiment of the method, image data of the examination region is provided with the aid of the tomography scanner. At least one section of a reference vessel permeated by contrast agent is selected in the image data. The image data is normalized on the basis of image data from the section of the reference vessel such that the contrast in the image data as a result of the contrast agent is almost independent of patient-specific and examination-specific parameters in order to ensure that image data from different times can be compared.

20 Claims, 2 Drawing Sheets

METHOD AND TOMOGRAPHY SCANNER FOR NORMALIZING IMAGE DATA WITH RESPECT TO A CONTRAST IN THE IMAGE DATA PRODUCED BY A CONTRAST AGENT

PRIORITY STATEMENT

The present application hereby claims priority under 35 U.S.C. §119 on German patent application number DE 10 2008 021 835.9 filed Apr. 30, 2008, the entire contents of which is hereby incorporated herein by reference.

FIELD

At least one embodiment of the invention generally relates to a method for normalizing image data with respect to a contrast in the image data produced by a contrast agent. At least one embodiment of the invention also generally relates to a tomography scanner which is correspondingly configured for normalizing image data with respect to a contrast in the image data produced by a contrast agent.

BACKGROUND

In x-ray diagnostics, contrasts in image data are produced by different attenuation characteristics of the substances with respect to the x-ray radiation generated by an x-ray device. Organs, vessels or tumors have a similar attenuation characteristic compared to neighboring tissue structures and, as a result of the low contrast connected to this, cannot be examined precisely in the image data without undertaking further measures. It is for this reason that a contrast agent having a very different attenuation characteristic compared to the tissue is utilized in these cases in order to increase the contrast. Hence, tissue structures can indirectly be made visible via the distribution of the contrast agent in the acquired image.

For this purpose, a contrast agent is administered to the patient according to a predeterminable injection protocol before the examination commences, with the contrast agent spreading through the examination region via the cardiovascular system. The spreading of the contrast agent in the body of the patient is a highly dynamic process. The amount of contrast agent present in the examination region and the increased contrast in the image data produced by the contrast agent depend on a multiplicity of patient-specific and examination-specific parameters. By way of example, examination-specific influencing variables include the concentration of the substance by which the attenuation characteristic of the contrast agent is determined, the absolute amount of injected volume or the flow rate of the contrast agent during the injection itself. Moreover, the pervasion of contrast agent into the examination region also depends on the selected period of time between the injection and the scan for obtaining image data and on the position on the body of the patient at which the contrast agent is administered. By way of example, patient-specific parameters include the heart rate and/or the blood pressure of the patient at the time of the examination. Moreover, the dispersion behavior of the contrast agent can also change as a result of taking medication.

Tumor diagnostics has a particular significance in human medicine because tumor-like diseases represent the second highest cause of death in industrialized countries after diseases of the cardiovascular system. The crucial basis for fighting such diseases is exact diagnosis with regard to tumor grading (diagnosis of type) and tumor staging (spread). In tumor staging, image data is compared to other image data recorded in examinations at different times in order to analyze the spread of the diseased tissue. The period between subsequent examinations can be weeks, months or even years.

As a result of the previously described influencing variables in imaging using an x-ray tomography scanner and a contrast agent, it is generally difficult to provide analysis of the tumor spread velocity on the basis of a comparison of image data because subsequent examinations cannot be carried out under exactly the same examination conditions. Often, it is not possible for the medical practitioner undertaking the diagnosis to discern whether the observed changes in contrast in the image data can be traced back to cell growth or are due to the follow-up examination having changed patient-specific and/or examination-specific parameters.

SUMMARY

In at least one embodiment of the present invention, a method and a tomography scanner are specified, respectively, for normalizing image data with respect to a contrast in the image data produced by a contrast agent, by which it is possible to compare the contrast in the image data of subsequent examinations by simple structure.

At least one embodiment of the method is for normalizing image data with respect to a contrast in the image data produced by a contrast agent. At least one embodiment of the invention is also directed to a tomography scanner.

In the method according to at least one embodiment of the invention, image data to be normalized with respect to a contrast of an examination region in the image data produced by a contrast agent is provided with the aid of imaging diagnostic medical equipment. The image data of the examination region illustrates a tissue structure to be examined and at least part of a blood vessel system connected to the tissue structure, which are at least in part permeated by contrast agent. At least one section of a reference vessel permeated by contrast agent is selected from the blood vessel system illustrated in the image data. The image data is subsequently normalized on the basis of image data from the section of the reference vessel.

The inventors have recognized that comparing the contrast agent enhancement in image data between different examinations can be almost independent of the patient-specific and/or examination-specific parameters present in the examinations precisely when the image data is specified in relation to image data of a reference vessel, the reference vessel being selected from the blood vessel system which is connected to the tissue structure to be examined.

In general, it can be assumed that the blood vessel system does not change significantly in follow-up examinations. Geometric dimensions and connections of the vessels to the tissue structure to be examined are therefore basically identical at the time of every examination. Any change in the contrast of a vessel permeated by contrast agent in relation to the surroundings observed between the examinations can basically be traced back to a change in patient-specific and/or examination-specific parameters on account of this situation. Since the contrast agent pervades into the tissue structure to be examined and is removed therefrom again via the vessels, the contrasts observed in the vessels correlate with those inside the tissue structure. As a result of this existing correlation, it is possible to normalize the image data such that a contrast within the tissue to be examined produced by the contrast agent can be displayed almost independently of changes in patient-specific and/or examination-specific parameters. This is a result of the image data being specified in relation to the image data of a reference vessel.

The normalization according to at least one embodiment of the invention therefore in particular offers the advantage of the image data from different examinations becoming more comparable, despite different injection protocols and/or different heart rates of the patient, and the advantage of changes in the vascularization being able to be determined with a high quality for reliable diagnosis by a medical practitioner. Such a normalization makes geometric and perfusion-specific changes of the tissue structure to be examined immediately visible by comparing different examinations. By way of example, the tissue structure to be examined itself can be a vessel, an organ or a tumor.

It is preferable to select an artery which is fed to the tissue structure as the reference vessel because the contrast agent is supplied to the tissue structure through this vessel and the correlation is highest between the observed contrast in the region of the reference vessel and the contrast in the region of the tissue structure.

In one refinement of at least one embodiment of the invention, a reference value is first of all calculated which is representative of the contrast agent in the reference vessel. Subsequently, during the normalization, the image data is divided by the calculated reference value. The reference value can be calculated using low computational resources by averaging the image data or by applying a median filter to the image data.

In a further advantageous refinement of at least one embodiment of the invention, the normalization is additionally carried out with reference to at least one geometric parameter of the reference vessel. Geometric parameters have to be taken into account if the geometry of the reference vessel changes between two examinations. By way of example, in the case of a constriction or a widening of the reference vessel, the cross-sectional area of the reference vessel can be used as a geometric parameter to carry out an additional normalization. In the normalization, the image data can for example be divided by the cross-sectional area. Likewise, normalization by multiplying the image data by a normalizing factor would be feasible, the normalizing factor being formed by the ratio of two cross-sectional areas or their average values along a section of the reference vessel.

Methods from digital image processing are preferably utilized to select the reference vessel, with the result that the selection is basically carried out autonomously. Here, image processing can advantageously comprise image segmentation, in which at least part of the blood vessel system is segmented. Registering the blood vessel system segmented in this fashion to a blood vessel system model at the disposal of the diagnostic medical equipment furthermore advantageously affords the possibility of precise anatomical assignment of the blood vessels and selection of the reference vessel based on anatomical criteria. Hence, the arteries led to the tissue structure can easily be identified.

As an alternative to this, the reference vessel can be prescribed particularly easily interactively by user inputs, for example by a user using a mouse to select a vessel in the vessel tree in a 2D or 3D image displayed using the image data. The image coordinates of the reference vessel are preferably determined and saved for normalizing image data in a follow-up examination. This ensures that the normalization between different examinations is carried out using the same reference vessel section.

In an advantageous refinement, the image data is obtained from projections of the examination region which are acquired using different energy spectra of x-ray radiation. Every substance has a dependence between the energy of the x-ray radiation and the absorption which is characteristic for the substance. By evaluating projections of an examination region which were acquired at different x-ray radiation energies, it is hence possible to calculate image data which mirrors material-specific characteristics utilizing this dependence.

Thus, it is possible, for example, to carry out a dual-energy scan using a computed tomography scanner for acquiring high energy image data at 140 kV tube voltage and low energy image data at 80 kV tube voltage. Image data which illustrates the pure contrast agent enhancement can be calculated from the high-energy image data and the low-energy image data by way of an algorithm. In this case, contrast agent enhancement is understood to refer to the increase of the contrast in the image data with reference to the image surroundings produced by the contrast agent.

However, the image data record on which a normalization is based can also be obtained from a difference image between a first image data record without the use of contrast agent and a second image data record using contrast agent.

BRIEF DESCRIPTION OF THE DRAWINGS

Example embodiments of the invention and further advantageous refinements of the invention in accordance with the dependent claims are illustrated in the following schematic drawings, in which:

DETAILED DESCRIPTION OF THE EXAMPLE EMBODIMENTS

Figure 1:
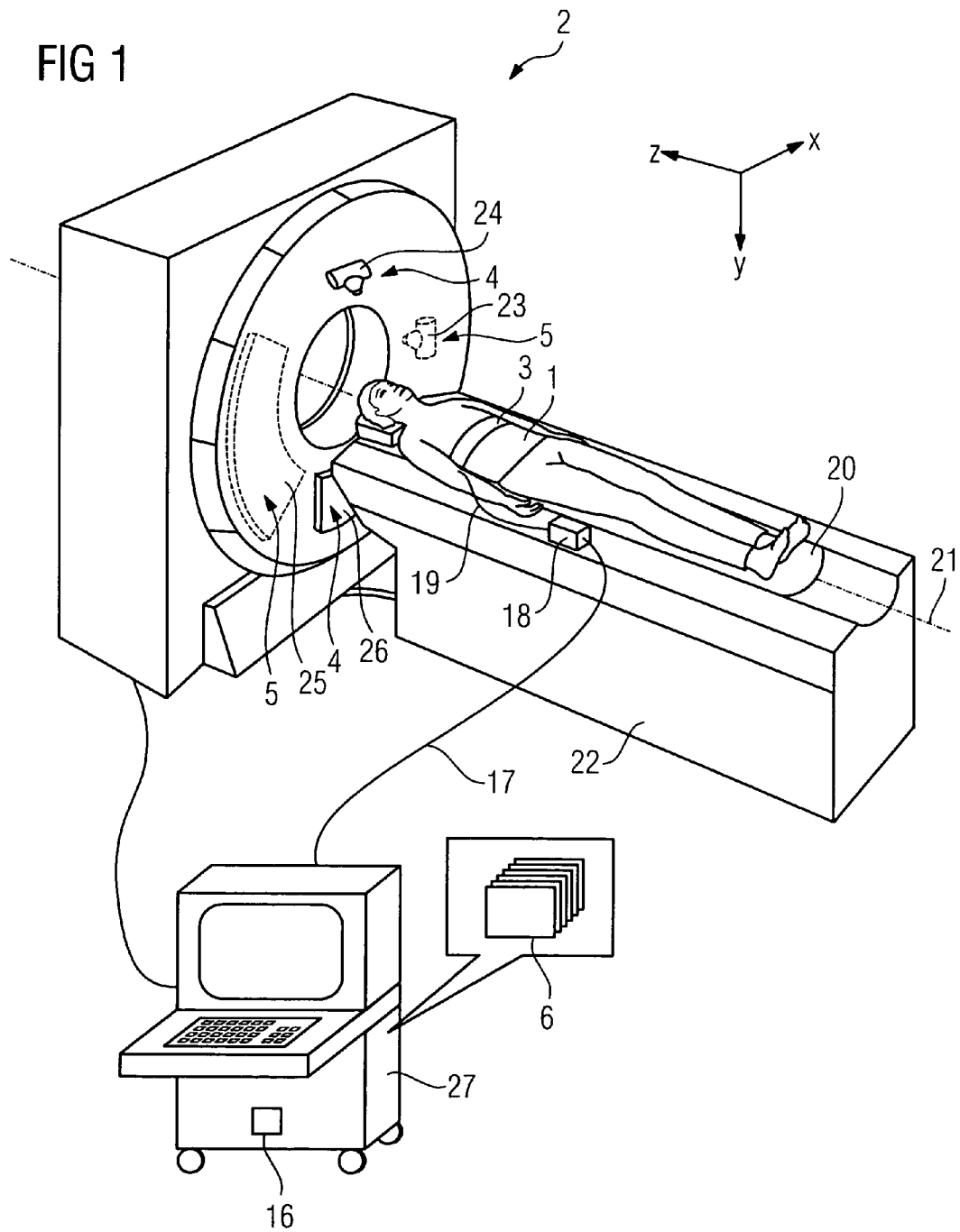
FIG. 1 shows, in a perspective view, a computed tomography scanner which is configured to carry out the method according to an embodiment of the invention for normalizing image data with respect to a contrast in the image data produced by a contrast agent.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows, in a perspective view, a tomography scanner, in this case a computed tomography scanner 2, which is configured for normalizing image data with respect to a contrast in the image data produced by a contrast agent.

Two recording systems 4, 5 are located in the interior of the computed tomography scanner 2 on a gantry (not illustrated) and are arranged rotatably around a system axis 21, by which recording systems projections of an examination region 3 can be acquired from a multiplicity of different projection directions. The two recording systems 4, 5 can be operated at different x-ray radiation energies so that by rotating the gantry, projections for generating a low-energy image and a high-energy image for material-specific examinations are acquired simultaneously. As an alternative to this, the recording systems 4, 5 can also be operated at the same x-ray radiation energy spectrum to increase the temporal resolution in the image data. The last-mentioned operating mode is suitable in particular for examining cyclically moving organs such as the heart or the lung.

A bearing apparatus 22 with a moveable tabletop 20 which bears the patient 1 is assigned to the computed tomography scanner 2. The tabletop 20 is arranged such that it can be adjusted in the direction of the system axis 21 of the computed tomography scanner 2 so that the examination region 3 in connection with the patient 1 can be moved through an opening in the housing of the gantry and into the measurement region of the two recording systems 4, 5.

In order to acquire projections, each recording system has an emitter in the form of an x-ray tube 23, 24 and a detector 25, 26 arranged opposite said tube, the detector 25, 26 being shaped like an arc and comprising a number of detector elements aligned to form detector rows. The x-ray tube 23, 24 generates radiation in the form of a fan-shaped x-ray beam bundle which penetrates the measurement region of the recording systems 4, 5. The x-ray radiation is subsequently incident on the detector elements of the detector 25, 26. The detector elements generate an attenuation value dependent on the attenuation of the x-ray radiation passing through the measurement region of the recording system 4, 5. The x-ray radiation is in each case converted into an attenuation value by way of, for example, a photodiode optically coupled to a scintillator or by way of a direct-conversion semiconductor.

The detector 25, 26 thus generates a record of attenuation values (CT values) which is recorded for the set projection direction of the recording system 4, 5. In the case of helical operation of the computed tomography scanner 2, a rotation of the gantry and a continuous feed of the patient 1 in the direction of the system axis 21 occur simultaneously. Thus, projections from a multiplicity of different projection directions are acquired at different positions along a helix around the examination region 3.

The projections of the recording system 4, 5 obtained by helical scanning are transferred to a computational unit 27 and are processed inline or in a processing step performed after the scanning procedure to form image data illustrating a slice image 6 or a volume image.

The projections obtained in a dual-energy operation of the computed tomography scanner 2 at two different x-ray radiation spectra, generated by way of example at 140 kV and 80 kV, are first of all processed to form a high-energy image and a low-energy image. An image can be calculated from the two images in which the image data does not represent pure CT values, but rather material-specific characteristics. In the case of a suitable composition, it is thus possible to image precisely that material with a high contrast in the image which basically fixes the attenuation characteristics of the contrast agent. In general, this will be iodine. An image generated in this manner is advantageously used for the normalization described below. However, it would likewise be conceivable to use a difference image as the basis for a normalization instead of a dual-energy image, the difference image being calculated from a native scan of the examination region without contrast agent and a scan with contrast agent. The contrasts in the difference image are then basically only produced by the contrast agent.

Contrast agent is always administered to the patient 1 if the contrast of perfused organs, vessels or other tissue structures such as tumors, visible in the image data, has to be increased compared to the surrounding tissue. An adjustable amount of contrast agent is pumped in a time-controlled manner and with an adjustable flow speed from a storage tank into, for example, the vein of the patient 1 via a contrast agent tube 19 by way of contrast agent equipment 18 in accordance with a prescribable injection protocol. In this case, the injection protocol at the disposal of the contrast agent equipment 18 is loaded from a memory 16 of the computational unit 27 via an electrical connection 17. Optionally, the injection protocol is selected from a database in which predefined, examination-specific injection protocols for the different examinations are stored. However, it would also be feasible for an operator to prescribe the parameters for administering the contrast agent directly before the start of the examinations by way of an operating unit of the computational unit 27.

The spread of the contrast agent in the interior of the body of the patient 1 is a highly dynamic process which depends on the examination-specific and/or patient-specific parameters present in the examination. Examination-specific parameters include, for example, the parameters prescribed in the injection protocol such as the flow rate of the contrast agent, the start time of the injection and the concentration of iodine in the contrast agent used. Patient-specific parameters include, for example, the heart rate and the blood pressure of the patient 1. Whereas examination-specific parameters in two subsequent examinations can to a certain extent be set to the same value, patient-specific parameters can only be controlled badly. By way of example, as a result of this, the findings do not make it possible to decide, from the results obtained within the scope of a tumor staging, whether an observed change in the contrast of the image data is produced by changes of the parameters or changes in the tissue.

In order to avoid this difficulty, a program is kept for disposal in the memory 16 which makes it possible to normalize image data with respect to a contrast in the image data produced by a contrast agent, so that after the normalization the image data record is largely independent of the examination-specific and/or patient-specific parameters present during the examination. Thus, the medical practitioner can assume that a change in contrast observed when comparing the image data is produced by tissue-specific changes, such as a change in cell growth.

Figure 2:
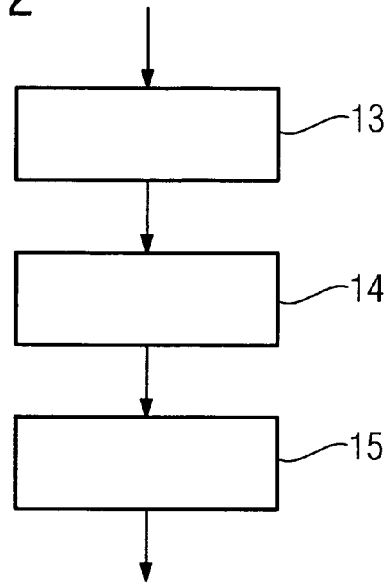
FIG. 2 shows a flowchart of the method according to an embodiment of the invention for normalizing the image data with respect to the contrast in the image data produced by the contrast agent.

FIG. 2 shows a flowchart for a method according to an embodiment of the invention for normalizing image data, the method steps of which are carried out on the computational unit 27 when the program is executed.

In a first processing step 13, the image data of the examination region is provided with the aid of imaging diagnostic medical equipment, in this exemplary embodiment with the aid of a computed tomography scanner.

In a second processing step 14, at least one section of a reference vessel permeated by contrast agent is selected from the image data.

In the process of selecting the reference vessel, it is obvious to select an artery led to the tissue to be examined because for such a vessel the correlation with respect to the observed contrast as a result of the contrast agent in the image region of the reference vessel and in the image region of the tissue to be examined is particularly high. Thus, the normalization which is carried out with reference to the reference vessel affords the possibility of eliminating those contrast effects in the tissue structure to be examined particularly well which cannot be traced back to a change in the tissue. However, the method could likewise be carried out by selecting other vessels. What is important in this case is that the administered contrast agent passes through the vessel. The decision as to which type of vessel and which section of the vessel is intended to be used as a reference could for example be made by a medical practitioner depending on the examination region.

The section of the reference vessel from the image data can subsequently be selected by using a digital image processing method. In order to find the section, the image data is classified according to the features by way of which the reference vessel can be represented. By way of example, characteristic features can include the contour, the profile of the contour, the grayscale distribution or the topological context.

The digital image processing method of at least one embodiment comprises segmenting at least part of the blood vessel system. In order to locate the reference vessel, the segmented blood vessel system is registered to a blood vessel system model at the disposal of the diagnostic medical equipment, the model also comprising information about anatomical assignment of the vessels or the vessel sections.

However, the section of the reference vessel can also be selected interactively in a different fashion, for example by way of a user input. In this simple and reliable method of selection, a medical practitioner can use a mouse, for example, to fix the vessel section of an image on a display unit, represented by the image data.

In order to ensure that the reference vessel can be found again during a follow-up examination, the image coordinates of the section and of the reference vessel are determined and are saved for the follow-up examination, for example together with the image data and possibly with further examination-specific and patient-specific parameters.

The image data is normalized in a third method step 15 on the basis of image data from the section of the reference vessel. A normalization which is easy to implement can include calculating a reference value which is representative of the contrast agent in the reference vessel and through which the image data will be divided. By way of example, the reference value can represent an average value or a median value of the image data located within the vessel. The limits of the vessel can be determined by gradient methods, so that an image region within the vessel can easily be defined for the evaluation.

In an ideal case, there are no changes of the reference vessel between subsequent examinations which change the perfusion characteristics so that a normalization only eliminates effects which are examination-specific or patient-specific. In the case where the vessel is expanded or constricted in a follow-up examination, it is possible for the normalization to additionally take account of a geometric parameter of the reference vessel, for example a cross-sectional area. For example, it would be possible to additionally multiply the image data by a calibration factor proportional to the cross-sectional area.

Figure 3:
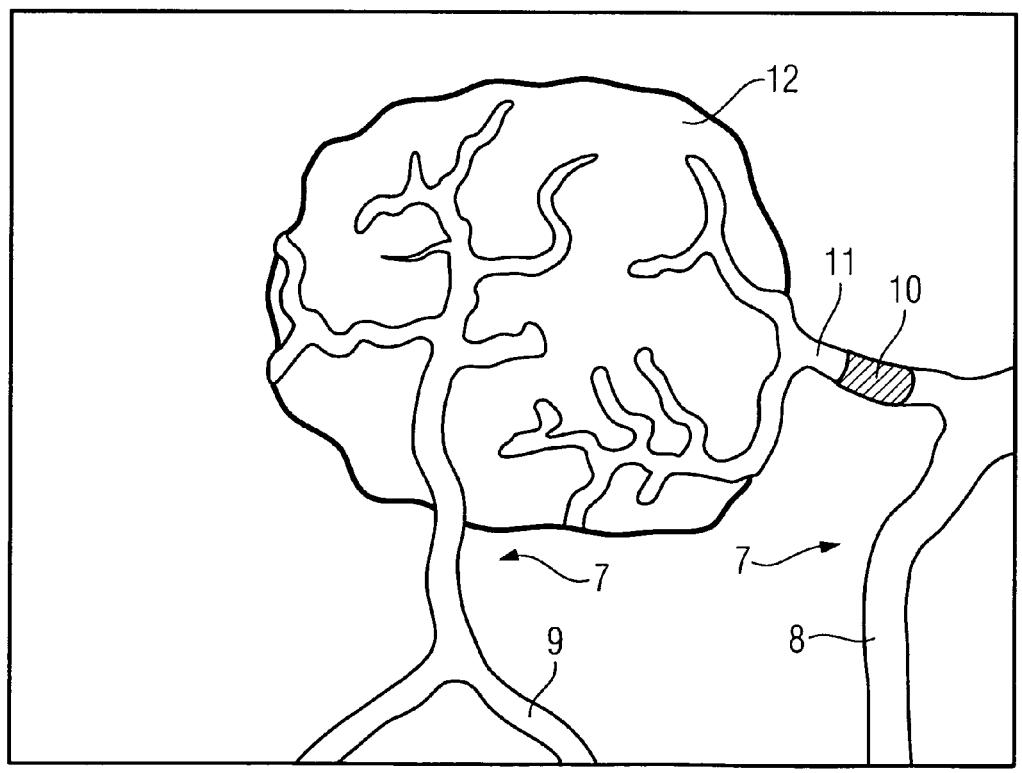
FIG. 3 shows a 2D image representation generated by the image data and showing the examination region with the selected section of a reference vessel.

FIG. 3 shows a 2D image representation which was generated by the image data and which shows the examination region 3 with a selected section 10 of a reference vessel 11. The illustrated examination region 3 comprises a tissue structure 12 to be examined, in this case a tumor, and part of a vessel system 7 connected to the tumor 12, with part of an artery 8 led to the tumor 12 and part of a vein 9 leading away from the tumor being visible. Moreover, the section 10 which was selected for normalizing the data record is marked.

The embodiments of the invention are, of course, not limited to only normalizing image data provided by a computed tomography scanner. It would likewise be feasible to apply the method to image data which is acquired by, for example, MRI, SPECT or ultrasound equipment.

An embodiment of the invention can be summarized as follows:

An embodiment of the present invention relates to a method and a correspondingly configured tomography scanner 2 for normalizing image data with respect to a contrast in the image data produced by a contrast agent, the image data illustrating a tissue structure 12 to be examined and at least part of a blood vessel system 7 of an examination region 3 connected to the tissue structure 12, which are at least in part permeated by the contrast agent. In the method, image data of the examination region 3 is provided with the aid of the tomography scanner 2. At least one section 10 of a reference vessel 11 permeated by contrast agent is selected in the image data. The image data is normalized on the basis of image data from the section 10 of the reference vessel 11 such that the contrast in the image data as a result of the contrast agent is almost independent of patient-specific and examination-specific parameters in order to ensure that image data from different times can be compared.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for normalizing image data with respect to a contrast in the image data produced by a contrast agent, the image data illustrating a tissue structure to be examined and at least part of a blood vessel system of an examination region connected to the tissue structure, which are at least in part permeated by the contrast agent, the method comprising:
   provisioning image data of the examination region with the aid of imaging diagnostic medical equipment;
   selecting at least one section of a reference vessel permeated by contrast agent from the blood vessel system illustrated in the provisioned image data; and
   normalizing the provisioned image data with respect to the contrast on the basis of image data from the selected at least one section of the reference vessel.

2. The method as claimed in claim 1, wherein the normalizing includes calculating a reference value, representative of the contrast agent in the reference vessel, and dividing the image data by the calculated reference value in the normalization.

3. The method as claimed in claim 1, wherein an artery, which is fed to the tissue structure, is selected as the reference vessel.

4. The method as claimed in claim 1, wherein the normalization is additionally carried out with reference to a geometric parameter of the reference vessel.

5. The method as claimed in claim 4, wherein a cross-sectional area of the reference vessel is used as the geometric parameter.

6. The method as claimed in claim 1, wherein methods from digital image processing are utilized to select the reference vessel, resulting in the selection basically being carried out autonomously.

7. The method as claimed in claim 6, wherein the digital image processing comprises image segmentation, in which at least part of the blood vessel system is segmented.

8. The method as claimed in claim 7, wherein the digital image processing comprises registering the segmented blood vessel system to a blood vessel system model at the disposal of the imaging diagnostic medical equipment.

9. The method as claimed in claim 1, wherein the reference vessel is selected interactively by way of user inputs.

10. The method as claimed in claim 1, wherein image coordinates of the reference vessel are determined and stored for a follow-up examination.

11. The method as claimed in claim 1, wherein the image data is obtained on the basis of projections of the examination region which are acquired using different energy spectra of x-ray radiation.

12. The method as claimed in claim 11, wherein the projections are acquired at a low-energy spectrum and a high-energy spectrum.

13. The method as claimed in claim 1, wherein the image data is obtained from a difference image between a first record of image data without the use of contrast agent and a second record of image data using contrast agent.

14. A tomography scanner, comprising:
a computational unit including a memory with a program code, wherein the program code is configured for normalizing image data with respect to a contrast in the image data produced by a contrast agent, according to the method of claim 1.

15. The method as claimed in claim 2, wherein an artery, which is fed to the tissue structure, is selected as the reference vessel.

16. The method as claimed in claim 2, wherein the normalization is additionally carried out with reference to a geometric parameter of the reference vessel.

17. The method as claimed in claim 16, wherein a cross-sectional area of the reference vessel is used as the geometric parameter.

18. The method as claimed in claim 2, wherein the image data is obtained on the basis of projections of the examination region which are acquired using different energy spectra of x-ray radiation.

19. The method as claimed in claim 18, wherein the projections are acquired at a low-energy spectrum and a high-energy spectrum.

20. A tangible computer readable medium including program segments for, when executed on a computer device, causing the computer device to implement the method of claim 1.

* * * * *